United States Patent
Burbano et al.

(10) Patent No.: US 10,077,476 B2
(45) Date of Patent: Sep. 18, 2018

(54) PROCESS AND MOLECULAR BIOMARKER

(71) Applicants: UNIVERSIDADE FEDERAL DO PARA—UFPA, Belem-Para (BR); CENTRO DE HEMOTERAPIA E HEMATOLOGIA DO PARA—HEMOPA, Belem-Para (BR)

(72) Inventors: Rommel Mario Rodriguez Burbano, Belem-Para (BR); Thais Brilhante Pontes, Belem-Para (BR); Leticia Martins Lamarao, Belem-Para (BR); Caroline De Fatima Aquino Moreira Nunes, Belem-Para (BR)

(73) Assignees: UNIVERSIDADE FEDERAL DO PARA-UFPA (BR); CENTRO DE HEMOTERAPIA E HEMATOLOGIA DO PARA—HEMOPA (BR)

( * ) Notice: Subject to any disclaimer, the term of this patent is extended or adjusted under 35 U.S.C. 154(b) by 0 days.

(21) Appl. No.: 15/326,972

(22) PCT Filed: Jul. 13, 2015

(86) PCT No.: PCT/BR2015/050090
§ 371 (c)(1),
(2) Date: Jan. 17, 2017

(87) PCT Pub. No.: WO2016/008020
PCT Pub. Date: Jan. 21, 2016

(65) Prior Publication Data
US 2017/0204464 A1    Jul. 20, 2017

(30) Foreign Application Priority Data

Jul. 14, 2014  (BR) .............................. 102014021701

(51) Int. Cl.
*C12Q 1/68* (2018.01)
*C12Q 1/6883* (2018.01)

(52) U.S. Cl.
CPC ..... *C12Q 1/6883* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

2007/0050146 A1   3/2007   Bentwich et al. .............. 702/19

OTHER PUBLICATIONS

Stratz et al (Thrombosis and Haemostasis 111: 902-911, published online Dec. 19, 2013).*
Nagalla et al (Blood, 117(12): 5189-5197, 2011).*
Osman et al (Platelets, Sep. 2011; 22(6): 433-441) (Year: 2011).*
Osman et al (Platelets, Sep. 2011; 22(6): supporting Table 1 (Year: 2011).*
Moltzahn et al (Cancer Res; 71(2); 550-60, 2010) (Year: 2010).*
Tang et al (Nucleic Acids Research, 2006, vol. 34, No. 2 e9, 7 pages (Year: 2006).*
Tang et al (Nucleic Acids Research, 2006, vol. 34, No. 2 e9, supporting material) (Year: 2006).*
Roberts et al (Plos One 9(2): e8237, 2014) (Year: 2014).*
Landry et al (Nature Structural Biology 16(9): 961-967, 2009) (Year: 2009).*
Landry et al (Nature Structural Biology 16(9), 2009 Supplementary Information File) (Year: 2009).*
Edelstein et al., "Small RNAs as Potential. Platelet Therapeutics," Handbook of Experimental Pharmacology, vol. 210, pp. 435-445, abstract only (6 pgs).
Holme, S., "In vitro assays used in the evaluation of the quality of stored platelets: Correlation with in vivo assays," Transfusion and Apheresis Science, vol. 39, No. 2, Sep. 2008, pp. 161-165, abstract only (4 pgs).
International Search Report (w/translation) issued in application PCT/BR2015/050090, dated Oct. 23, 2015 (8 pgs).
Kannan et al., "Membrane array-based differential profiling of platelets during storage for 52 miRNAs associated with apoptosis," Transfusion, vol. 49, No. 7, Jul. 2009, pp. 1443-1450, abstract only (3 pgs).
Kulkarni et al., "Omic Approaches to Quality Biomarkers for Stored Platelets: Are We There Yet?" Transfusion Medicine Reviews, vol. 24, No. 3, Jul. 2010, pp. 211-217, abstract only (2 pgs).
Osman et al., "Characterization of human platelet microRNA by quantitative PCR coupled with an annotation network for predicted target genes," Platelets, vol. 22, No. 6, 2011, pp. 433-441, abstract only (6 pgs).
Schubert et al., "Towards targeting platelet storage lesion-related signaling pathways," Blood Transfus, vol. 8, suppl. 3, 2010, pp. 69-72 (4 pgs).

* cited by examiner

*Primary Examiner* — Richard A Schnizer
(74) *Attorney, Agent, or Firm* — Hayes Soloway P.C.

(57) ABSTRACT

A process and molecular biomarker for platelets stored in blood banks provides for efficient verification of which platelet concentrate bags are in good condition for transfusion by measuring, by real-time polymerase chain reaction, expression levels of hsa-miR-127 and hsa-miR-320a microRNAs as the first process and biomarker predictor of platelet's cell aging during storage and the consequent presence of storage lesions as a quality test of these bags.

1 Claim, No Drawings

PROCESS AND MOLECULAR BIOMARKER

BACKGROUND OF THE INVENTION

The process and molecular biomarker refer to a process of detection and quantification of the expression of hsa-miR-127 and hsa-miR-320a microRNAs in platelets, specifically in platelets stored in a blood bank, as a means of ascertaining the aging cell process during the storage period and consequent presence of storage lesions, disabling the platelet concentrate bags to the donation.

The bags of platelet concentrates stored in blood banks at the present time are discarded after five days because there are no rapid quality tests that can detect the presence of storage lesions in these bags and the consequent cell aging and quality of the transfusion bags.

In the absence of a quality test, the use of bags stored for periods longer than five days would be a risk to patient's health. However, discarding all bags that reach this deadline may compromise blood bank platelet stores.

SUMMARY OF THE INVENTION

The molecular biomarker efficiently verifies which platelets concentrate bags are in good condition for transfusion, increasing the reliability in the quality of the platelet concentrate bags and reducing waste. This process will quantify by real-time polymerase chain reaction the concentration of the hsa-miR-127 and hsa-miR-320a microRNAs and through the mir127/320a relation will determine the quality of the bags, thus ensuring greater patient safety.

DETAILED DESCRIPTION OF THE INVENTION

The process and molecular biomarker for platelets stored in blood banks consists of isolating the hsa-miR-127 and hsa-miR-320a microRNAs from a small sample of each bag selected for transfusion, followed by quantification of the expression of these microRNAs. The quantitative relationship between these two microRNAs determines the quality of the stored platelets. Bags whose expression of hsa-miR-127 is greater than or equal to the expression of hsa-miR-320a will be suitable for transfusion. However, bags where the expression of hsa-miR-127 is less than the expression of hsa-miR-320a should be discarded because they are not safe for transfusion.

The invention claimed is:

1. A method for determining the suitability of stored, concentrated platelets for donation, comprising the steps of:
    isolating hsa-miR-127 and hsa-miR-320a microRNAs from a sample of the stored platelets,
    measuring an expression of the isolated hsa-miR-127 and the isolated hsa-miR-320a microRNAs using real-time polymerase chain reaction, and
    determining a ratio of the hsa-miR-127 and the hsa-miR-320a microRNAs based on said measurements,
    wherein when the expression of hsa-miR-127 is determined to be equal to or more than the expression of hsa-miR-320a, the platelets are employed for transfusion, and when the expression of hsa-miR-127 is determined to be less than the expression of hsa-miR-320a, the platelets are discarded.

* * * * *